(12) United States Patent
Booker

(10) Patent No.: US 10,736,766 B2
(45) Date of Patent: Aug. 11, 2020

(54) BACK BRACE DEVICE

(71) Applicant: Lori Booker, Essex, MD (US)

(72) Inventor: Lori Booker, Essex, MD (US)

( * ) Notice: Subject to any disclaimer, the term of this patent is extended or adjusted under 35 U.S.C. 154(b) by 409 days.

(21) Appl. No.: 15/212,261

(22) Filed: Jul. 17, 2016

(65) Prior Publication Data

US 2017/0014255 A1 Jan. 19, 2017

Related U.S. Application Data

(60) Provisional application No. 62/193,758, filed on Jul. 17, 2015.

(51) Int. Cl.
*A61F 5/02* (2006.01)
*A61F 5/34* (2006.01)
*A61F 7/03* (2006.01)
*A61F 7/02* (2006.01)

(52) U.S. Cl.
CPC ............... *A61F 5/028* (2013.01); *A61F 5/34* (2013.01); *A61F 7/03* (2013.01); *A61F 2007/0228* (2013.01)

(58) Field of Classification Search
CPC .. A61F 5/028; A61F 5/02; A61F 5/022; A61F 5/024; A61H 2201/165; A61H 2201/1652; A61H 2201/1654; A61H 2205/08; A61H 2205/081
See application file for complete search history.

(56) References Cited

U.S. PATENT DOCUMENTS

| | | | | |
|---|---|---|---|---|
| 5,378,225 A | * | 1/1995 | Chatman, Jr. | A61F 5/028 219/480 |
| 5,628,721 A | * | 5/1997 | Arnold | A61F 5/028 128/118.1 |
| 5,827,209 A | * | 10/1998 | Gross | A61B 5/1121 602/19 |
| 2013/0331755 A1 | * | 12/2013 | Rotblatt | A61F 5/028 602/19 |

* cited by examiner

*Primary Examiner* — Kari K Rodriquez
(74) *Attorney, Agent, or Firm* — Howard University School of Law

(57) ABSTRACT

The present invention provides a device that provides relief for lower back pain and corrects bad posture. The back brace device comprises a plurality of belts having a rear side, a front side, and a first end removably securable to a second end. The rear side of at least one of the belts has an inflatable bladder that is controlled by an air pump. The device further comprises having a heating element and a vibration mechanism that can be turned on or off as desired by the user. The present invention is used by placing the belt around the waist of the user and securing the first and second ends to one another via one or more suitable fasteners. The bladder is then inflated in order to provide support to the back of the user.

11 Claims, 10 Drawing Sheets

BACK BRACE DEVICE

CROSS-REFERENCES TO RELATED APPLICATIONS (IF ANY)

This application claims the priority date of Provisional Application No. 62/193,758 filed on Jul. 17, 2015.

BACKGROUND

1. Field of the Invention

The invention relates generally to back brace, and in particular to one the helps correct back posture.

2. Description of Prior Art

Conventional back braces that are currently used to correct back posture do not provide relief from lower back pain and pressure. Some individual apply a heating pad or a cold compress to their lower back in order to provide temporary relief. However, these techniques are ineffective if the individual also desire to simultaneously correct his or her back posture.

There is still room for improvement in the art.

SUMMARY OF THE INVENTION

The present invention is a back brace device that provides relief for lower back pain and corrects bad posture providing the just correct alignment.

The back brace device comprises a dual belt having a rear side, a front side, and a first end that is securable to a second end. The rear side of the inner belts has an inflatable bladders or tubes that are filled by an air pump. The belt has a heating element and a vibration mechanism that can be turned on or off as desired by the user. The device can also be done in a single belt.

The current invention is more efficient, effective, accurate and functional than the current art.

BRIEF DESCRIPTION OF THE DRAWINGS

Without restricting the full scope of this invention, the preferred form of this invention is illustrated in the following drawings.

DESCRIPTION OF THE PREFERRED EMBODIMENT

There are a number of significant design features and improvements incorporated within the invention.

The current invention is directed to back brace device 1 as shown in FIGS. 1-10.

Figure 12:
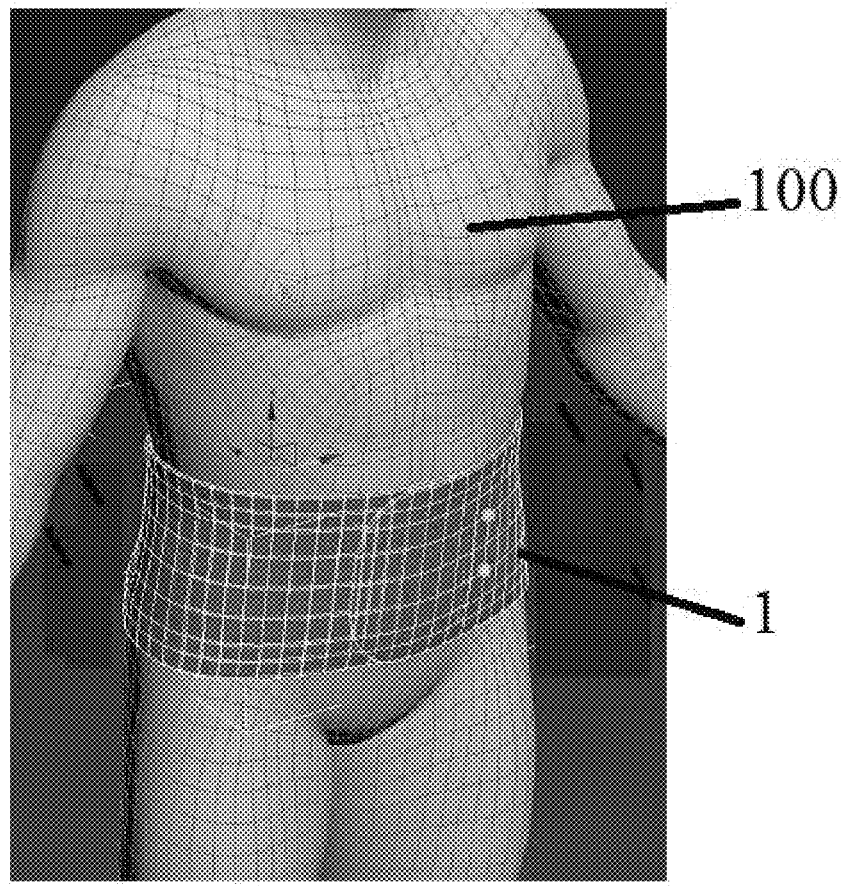
FIG. 12 display the device being used.

The back brace device 1 comprises an inner belt 10 and an outer belt 15 having a front side, a left side, a right side and a rear side. The belts, 10 and 15, each have two ends which attached to each other using an attachment means 17 which in the preferred embodiment are hook and loop fasteners. The device 1 and the belts are adapted to form a loop configuration around a user's lumber and coccyx region as shown in FIG. 12. The attachment means 17 will allow the belts to be adjustable to fit the user. The dual belt system allows for a better fit and more support for the user however a single belt could be used with all the same elements.

The back brace device 1 further comprises one or more bladders 20 disposed along the length of the rear side of the inner belt 10. Each bladder 20 is adapted to be inflated with air via three air pump 30 which are located in the middle rear of the outer belt 15. The bladders 20 are tube shaped in the preferred embodiment. Thus, the inflated bladders 20 provide back support for the user 100. The bladders 20 are connected to each other so that the air and pressure is evenly distributed. The back brace device 1 further comprises a pressure sensor 25 that is adapted to automatically activate the air pumps 30 if the air pressure in the bladders falls below a predetermined level which can be set by the user 100.

Figure 6:
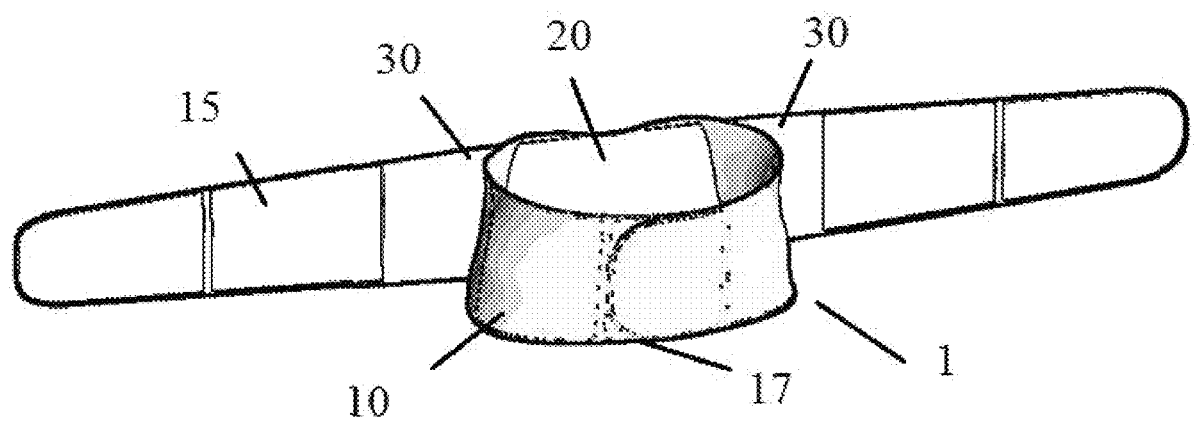
FIG. 6 shows the outer belt open and the inner belt closed.
Figure 7:
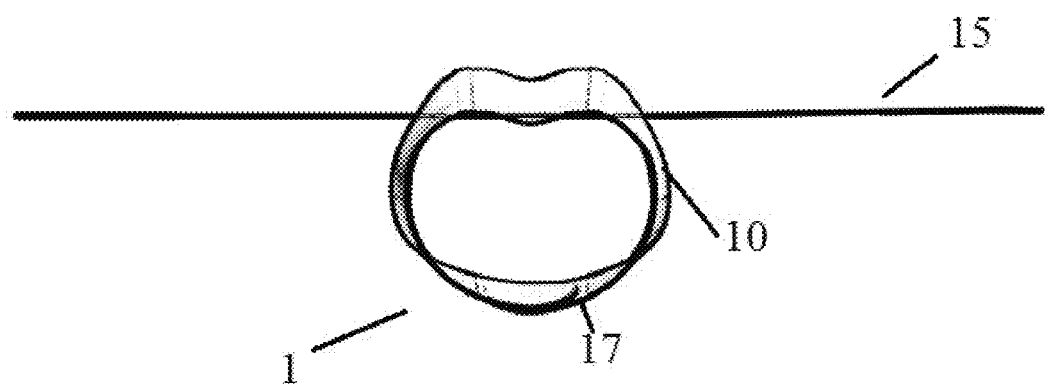
FIG. 7 shows a top view of the outer belt open and the inner belt closed.
Figure 8:
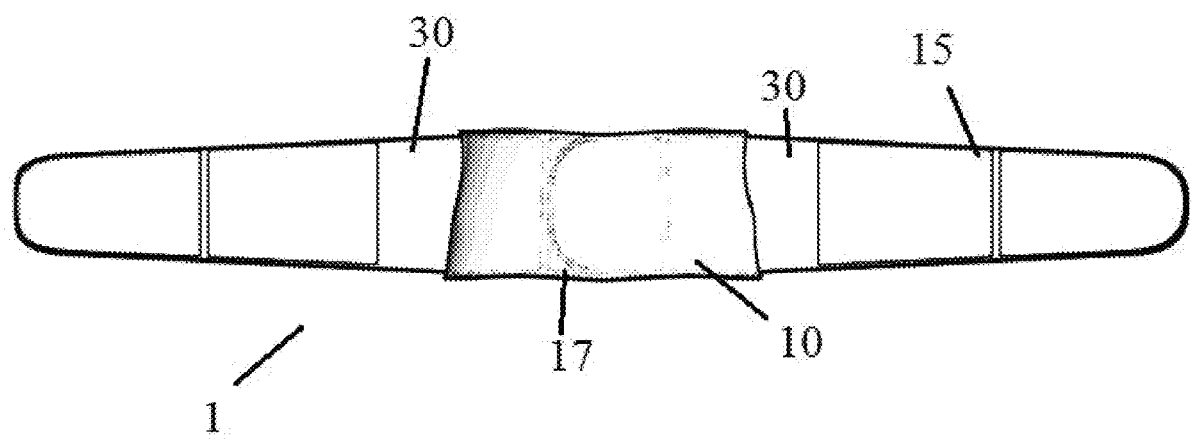
FIG. 8 shows a front view of the outer belt open and the inner belt closed.
Figure 9:
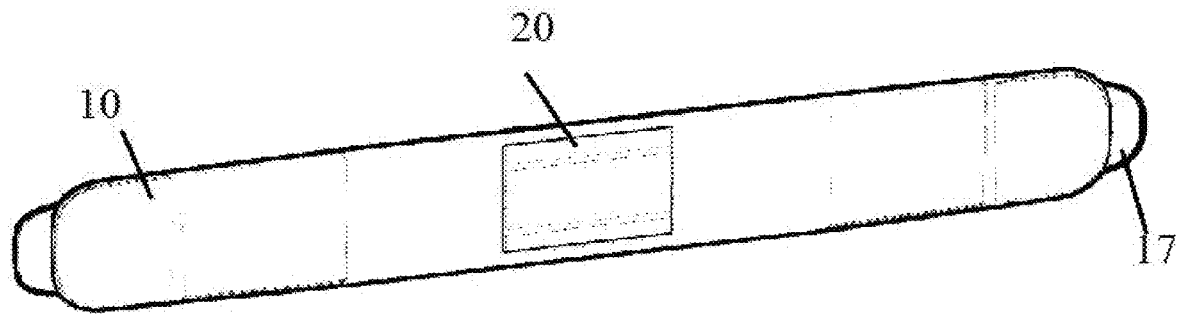
FIGS. 9 and 10 show the outer belt open.
Figure 10:
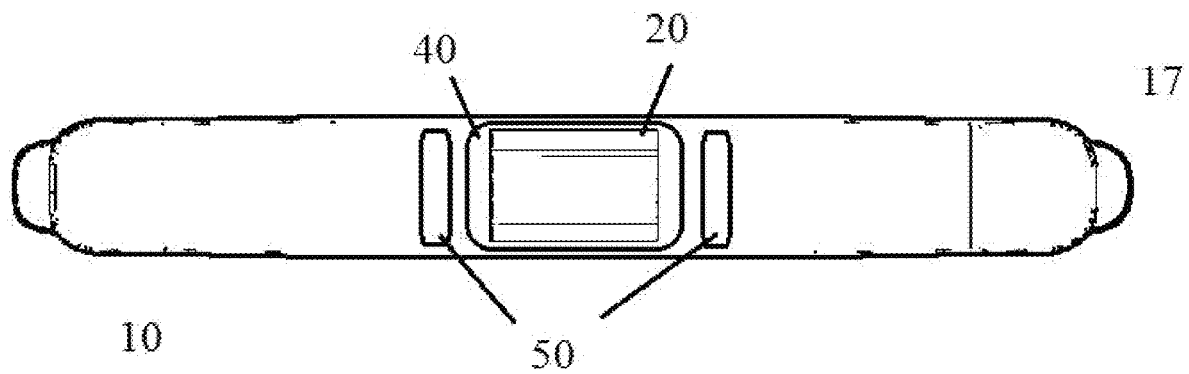
Figure 11:
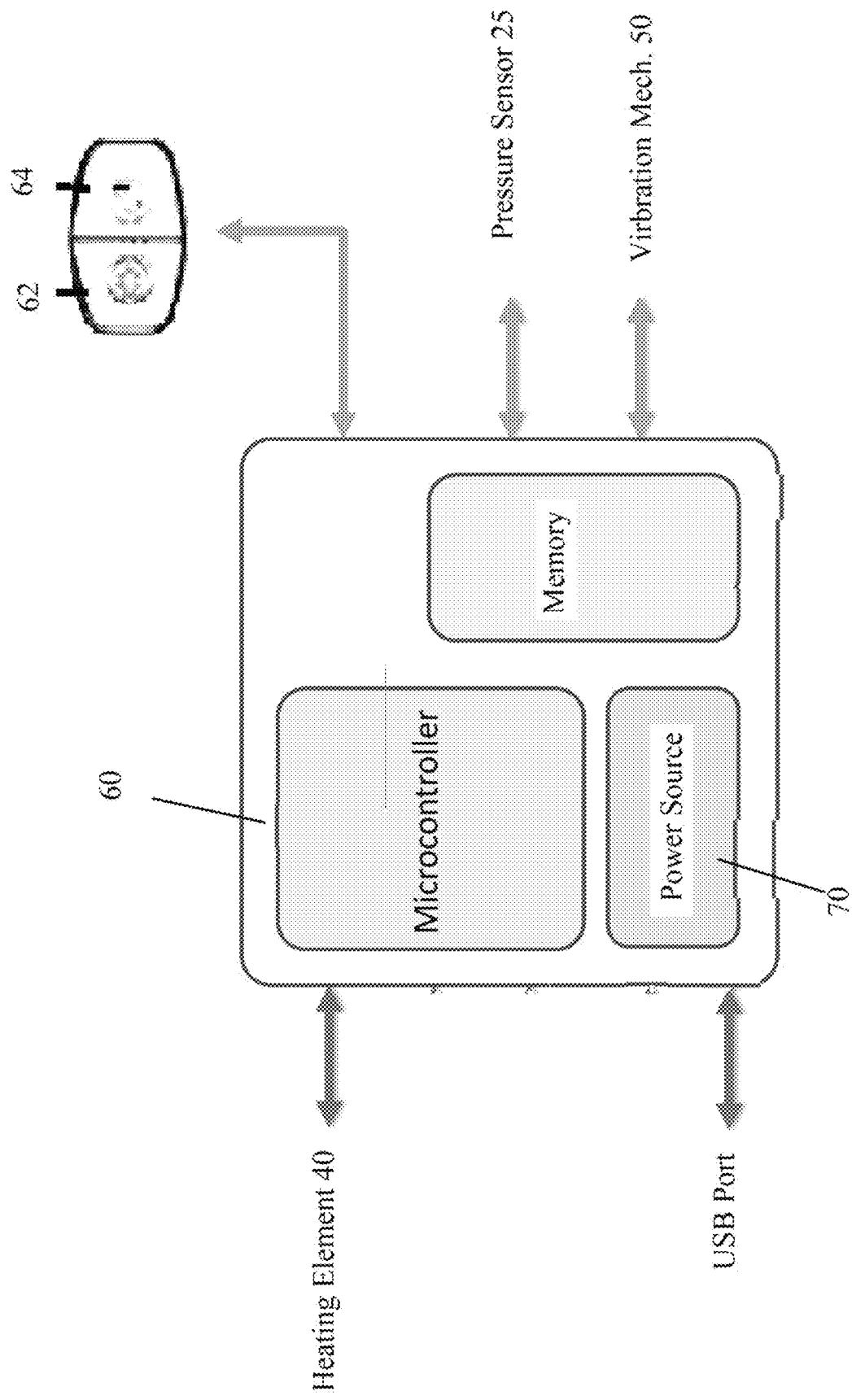
FIG. 11 displays the components of the device.

The inner belt 10 and the outer belt 15 are connected in the rear of the belts as shown in FIGS. 6 and 7. The inner belt 10 wraps around the user 100 and the outer belt 15 wraps around the inner belt 10 adding additional support.

Figure 1:
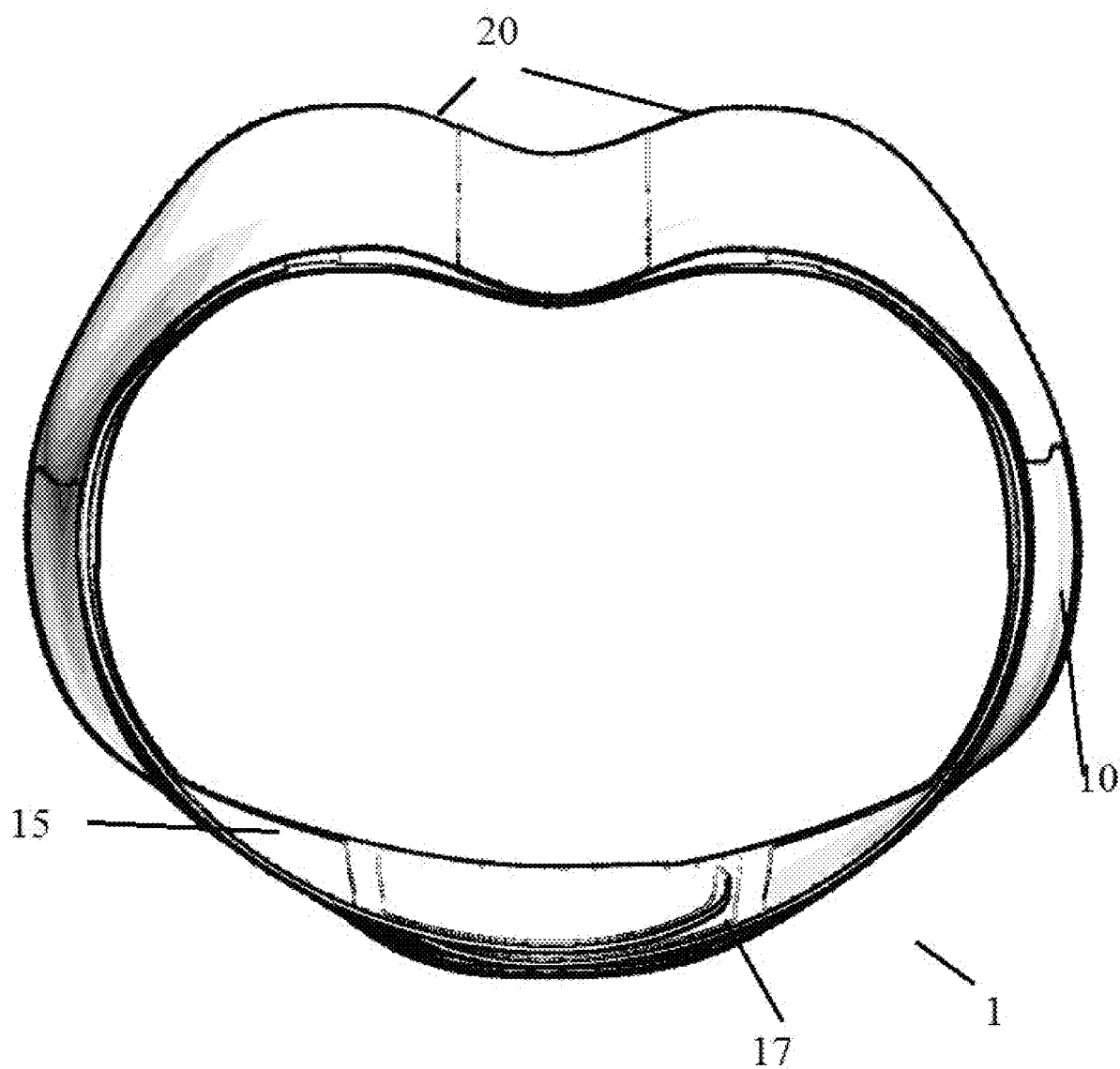
FIG. 1 shows a top view of the belts.
Figure 2:
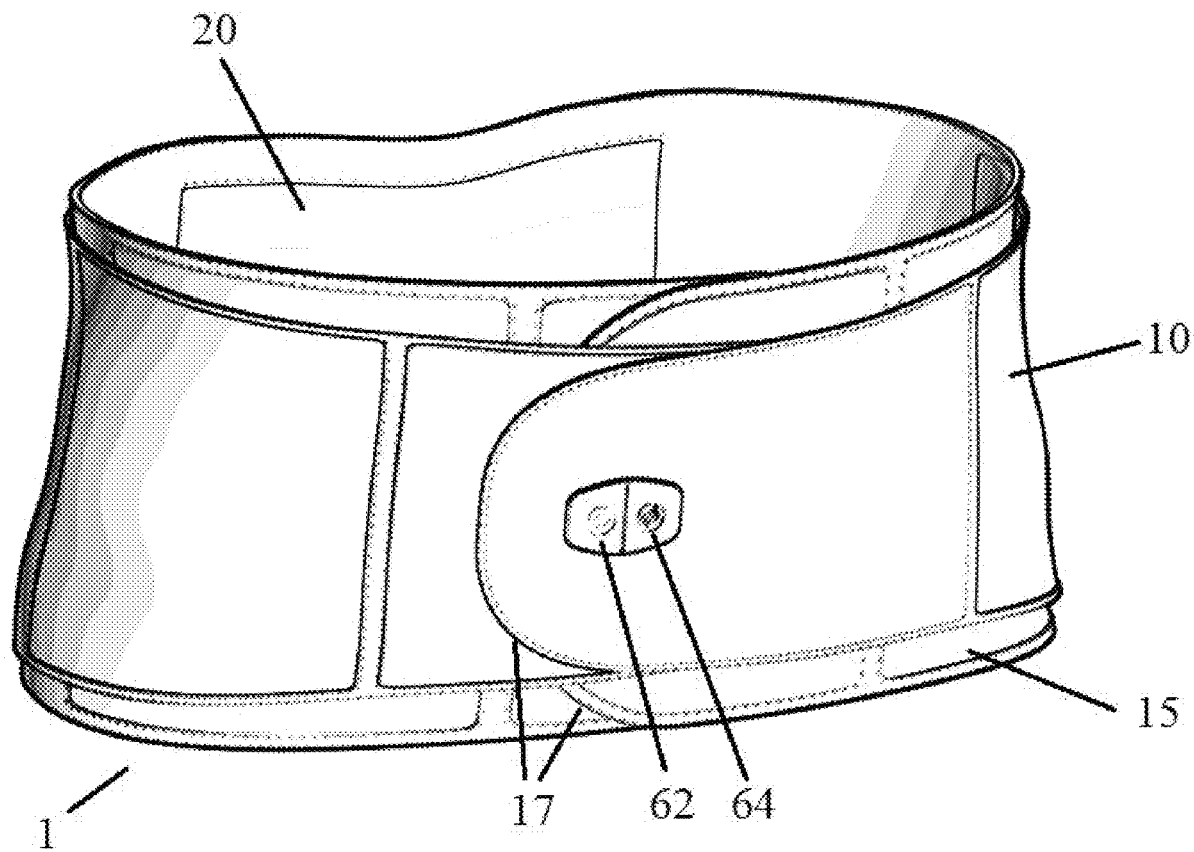
FIG. 2 shows a front right view of the belts.
Figure 3:
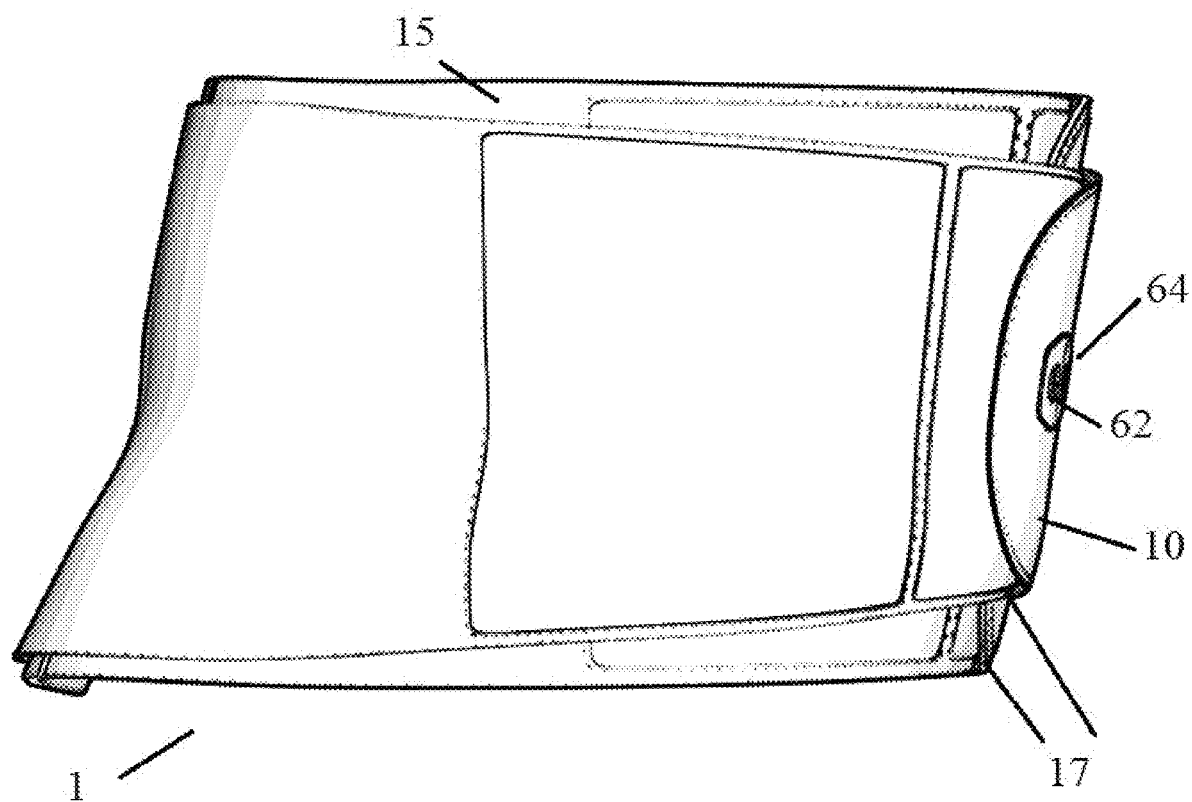
FIG. 3 shows a side view of the belts.
Figure 4:
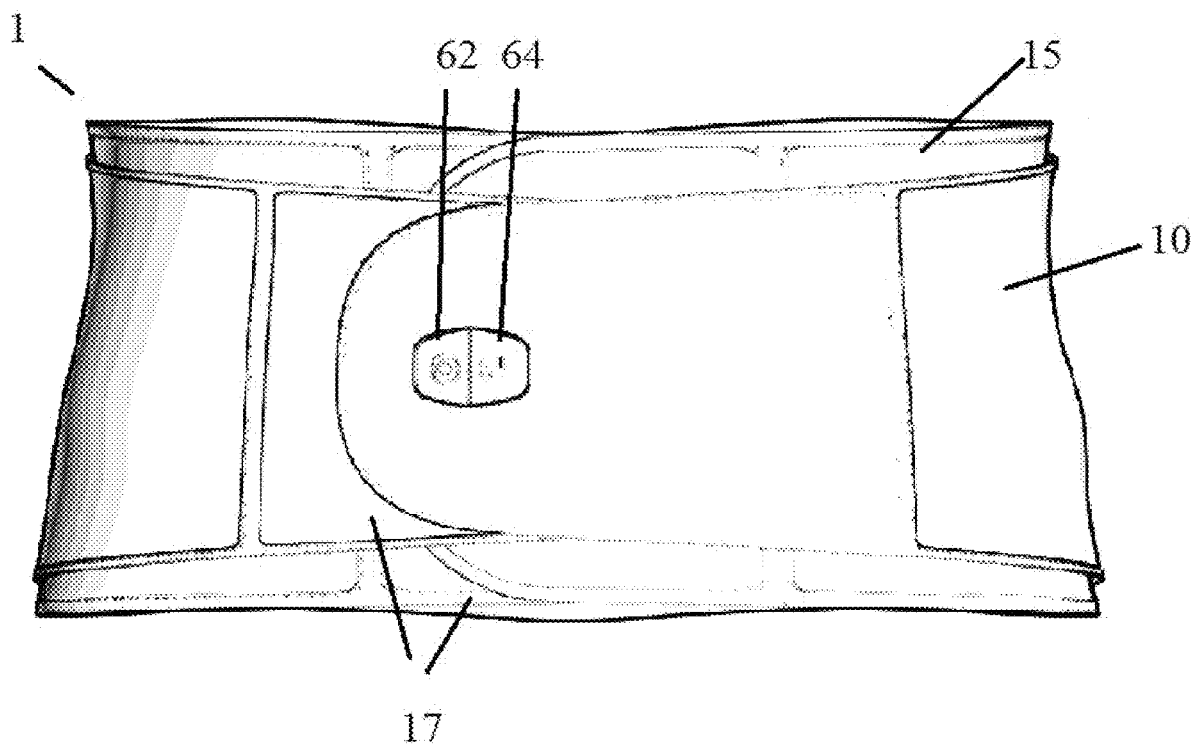
FIG. 4 shows a front view of the belts.
Figure 5:
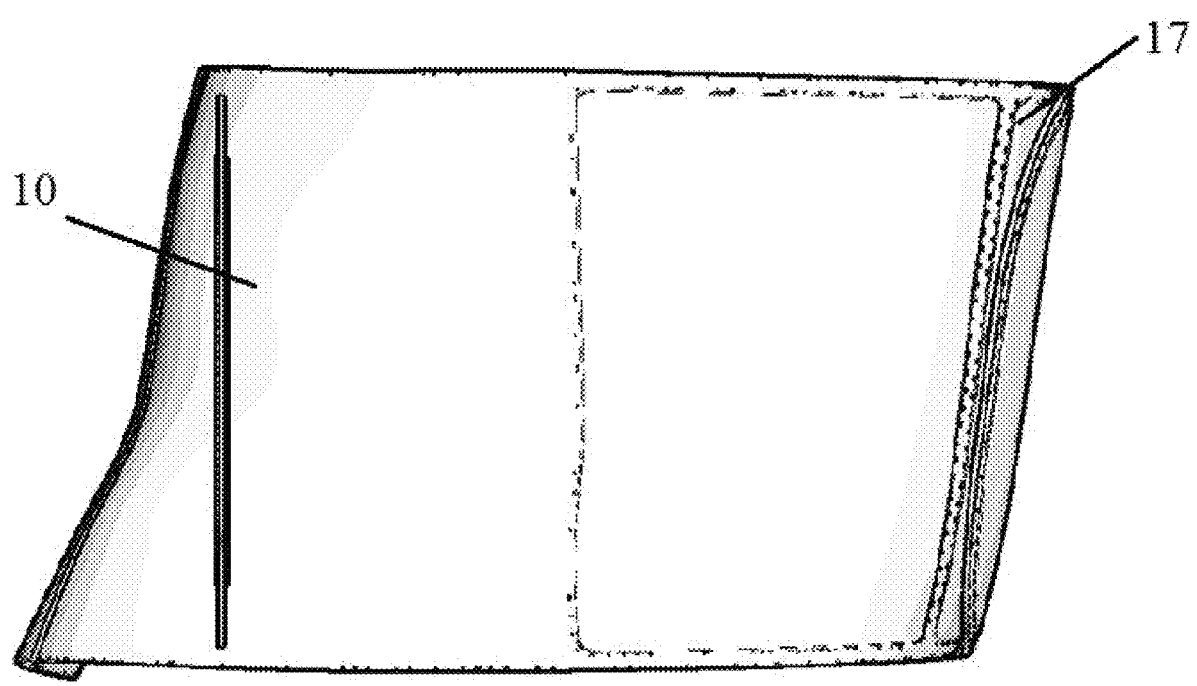
FIG. 5 shows a side view of the inner belt.

The belts further house a heating element 40 and a vibration mechanism 50 to relieve back pain and stress. As shown in FIGS. 2 and 4, the device 1 will have control buttons on the front of the outer belt 15. These buttons, heat control button 62 and vibration control button 64, will control the heating element 40 and the vibration mechanism 50 and in the preferred embodiment each have three levels of variance between light heat, light vibration up to heavy heat, heavy vibration. In alternative embodiments, there could be a button to control the air pumps 30. These buttons are connected to a control circuit 60.

The control circuit 60 and power source 70 is positioned along the outer belt 15, wherein the control circuit 60 is operably connected to the power source 70, heating element 40, air pump 30, pressure sensor 25 and vibration mechanism 50. In the preferred embodiment the power source is batteries. The control circuit 60 will a means to turn on and off the heating element 40, air pump 30 and vibration mechanism 50. The power source 70 can be a rechargeable battery that is rechargeable through a USB port. A USB port can also be connected to the control circuit 60. The control circuit 60 would consist of a microprocessor and electronic memory.

The belts are made of a strong, light weight material such as nylon or nylon mesh designed to have a proper fit on a user's back.

Advantages

The current invention is a lower back brace that helps alleviate stress and pressure on the back, significantly decreasing pain in the lumbar region. The design features the following benefits that cannot be replicated by other back braces; provides relief from lower back pressure, enhances stability in the upper and lower torso, rests flush against the lower back with pressurized air tubes, relaxes the muscles with heat and vibrations for added relief, and helps people stand and sit with ease While the methods disclosed herein have been described and shown with reference to particular steps performed in a particular order, it is understood that these steps may be combined, sub-divided, or reordered to form an equivalent method without departing from the teachings of the embodiments. Accordingly, unless specifically indicated herein, the order and grouping of the steps is not a limitation of the embodiments. Furthermore, methods and mechanisms of the embodiments will sometimes be described in singular form for clarity. However, some embodiments may include multiple iterations of a method or multiple instantiations of a mechanism unless noted otherwise. For example, when a connection is disclosed in one embodiment, the scope of the embodiment is intended to also cover the use of multiple connections.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

That which is claimed is:

1. A back brace device adapted to be worn on a human body, comprising:
    an inner adjustable belt having a front side, a rear side, a first distal end and a second distal end with a releasable fastening system that connects the first distal end and the second distal end together,
    the inner adjustable belt having a plurality of air bladders positioned along a length of the rear side,
    an outer belt that is placed over the inner belt having a plurality of pumps connected to the bladders, the outer belt having a distal outer belt first end, and a distal outer belt second end, wherein the distal outer belt first end and the distal out belt second end are adapted to be releasably fastened to each other,
    the inner adjustable belt and the outer belt being adapted to collectively form a loop configuration around a human body lumber and coccyx region;
    said device having a heating element, a vibration mechanism, a control circuit and a rechargeable power source,
    wherein the control circuit is operably connected to the heating element and the vibration mechanism;
    wherein the vibration mechanism includes a first vibration element disposed to one side of the air bladders and a second vibration element disposed to an opposing side of the air bladders;
    wherein the control circuit includes a microprocessor and a computer readable memory configured to control at least three levels of variance of heat and vibration from the heating element and vibration mechanism, respectively.

2. The back brace device according to claim 1, further comprising pressure sensor configured to measure a pressure of the air bladders; wherein the pressure sensor is operably connected to the control circuit.

3. The back brace device according to claim 2, further comprising the pressure sensor being configured to activate the air pump to pump air into the bladders when the measured air pressure is lower than a pre-set air pressure.

4. The back brace device according to claim 1, further comprising plurality of control buttons being operably connected to the control circuit, wherein the control buttons includes a vibration control button for controlling the vibration mechanism and a heat control button to controlling the vibration mechanism; wherein the control buttons are disposed on the outer belt adjacent to the one of the first distal end outer belt or the second distal end outer belt.

5. The back brace device according to claim 4, wherein the control buttons includes an air pump control button to control the air pumps.

6. The back brace device according to claim 1, further comprising the power source including a battery, the device further including a USB port connected to the control circuit and the power source.

7. The back brace device according to claim 1, wherein the control circuit is positioned along the outer belt.

8. The back brace device according to claim 7, wherein the power source is positioned along the outer belt.

9. The back brace device according to claim 7, wherein the heating element is disposed adjacent to the air bladders.

10. The back brace device according to claim 1, wherein the inner adjustable belt and the outer belt are constructed of a nylon material.

11. The back brace device according to claim 10, wherein the fastening system includes a hook and loop material.

* * * * *